United States Patent [19]

Buzzell

[11] 4,275,585
[45] Jun. 30, 1981

[54] VIBRATOR TYPE DENSITOMETER

[75] Inventor: Colby E. Buzzell, Wilmington, Mass.
[73] Assignee: General Electric Company, Wilmington, Mass.
[21] Appl. No.: 97,038
[22] Filed: Nov. 21, 1979
[51] Int. Cl.³ .............................................. G01N 9/00
[52] U.S. Cl. .................................................. 73/32 A
[58] Field of Search ........................ 73/32 A, 32 R, 30

[56] References Cited
U.S. PATENT DOCUMENTS

| | | | |
|---|---|---|---|
| 3,225,588 | 12/1965 | Moulin et al. | 73/32 A |
| 3,690,147 | 9/1972 | Kuenzler | 73/32 A |
| 4,129,031 | 12/1978 | Tehon et al. | 73/32 A |

Primary Examiner—James J. Gill
Attorney, Agent, or Firm—I. David Blumenfeld

[57] ABSTRACT

A densitometer of the vibrator type is disclosed wherein a spring mass system is immersed in a liquid whose density is to be determined. The system includes a pair of coaxial cylindrical masses in the form of fluid couplers having spaces which are open to the liquid. A torsion spring connects both cylindrical masses through mechanically stiff coupling means. The coupling means include a pair of high impedance transducers positioned at the shear interfaces normal to the common axis of the system, so as to take substantially the full torsional shear load between the spring and the cylindrical fluid couplers without contributing to the spring effect. The compliance of the torsion spring allows oscillatory motion of the spring mass system around its axis. An output signal having a high signal-to-noise ratio is provided at the natural resonant system frequency. The signal frequency is a measure of the density of the liquid contained in the spaces and it is substantially independent of the effect of temperature changes on the transducers. Thus, a highly sensitive and accurate densitometer is provided.

16 Claims, 4 Drawing Figures

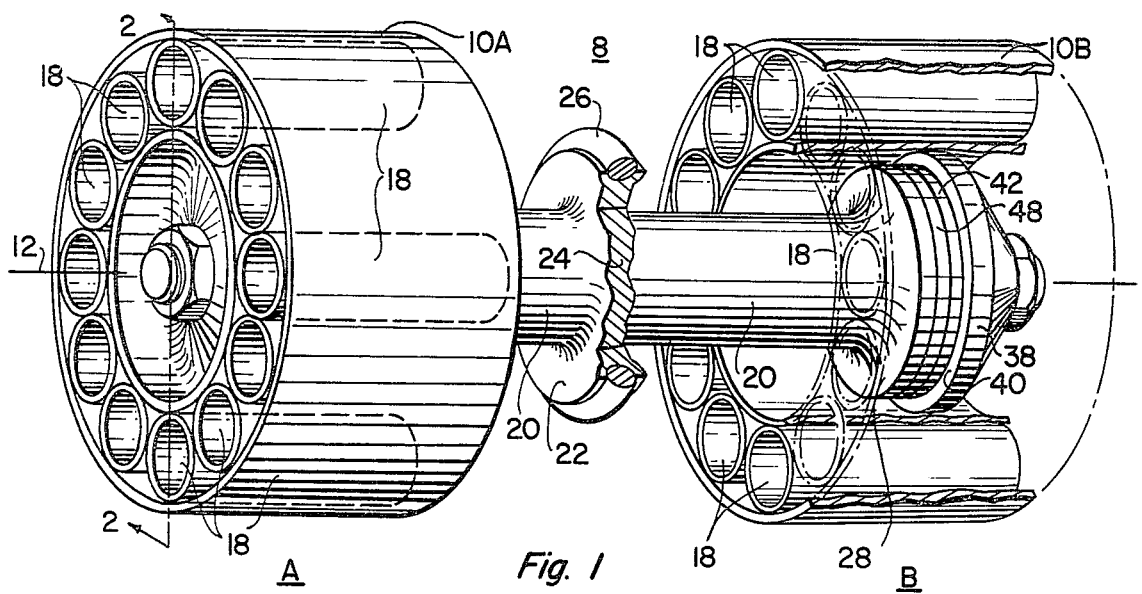
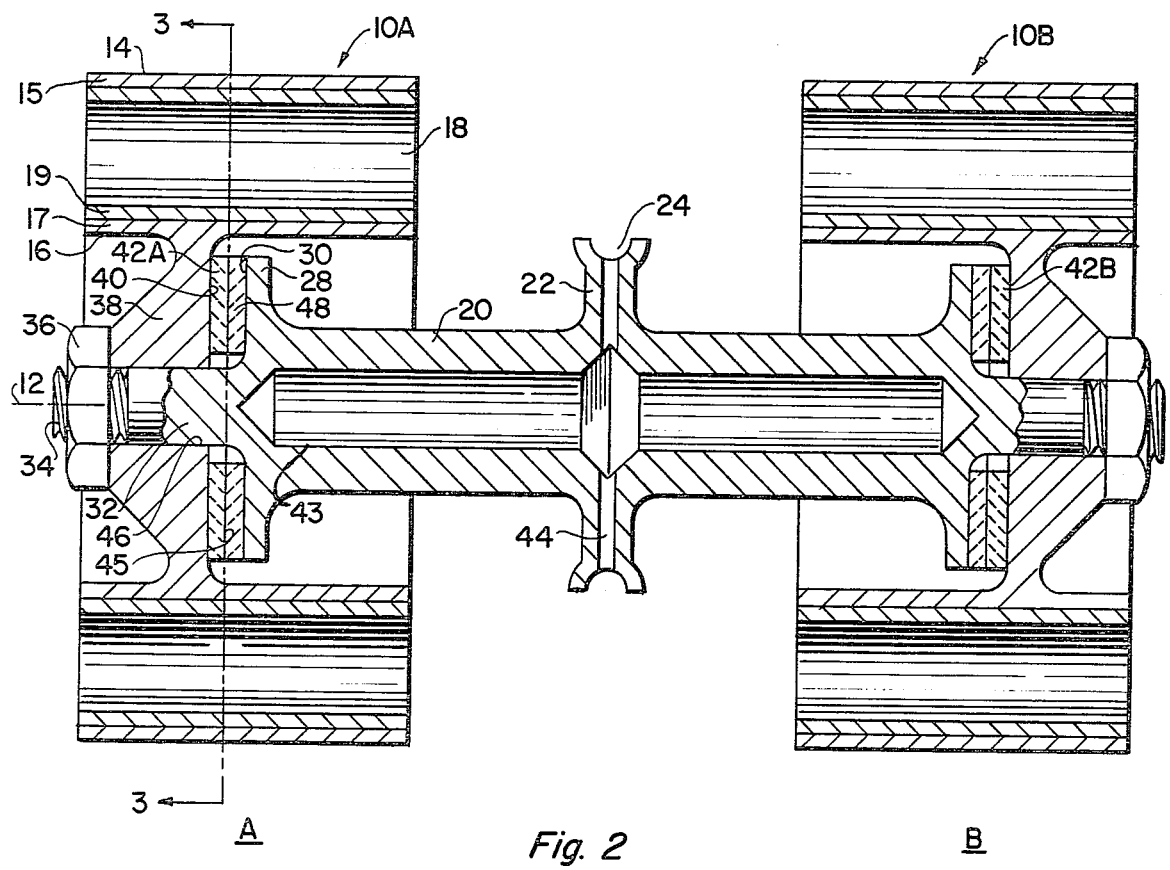

VIBRATOR TYPE DENSITOMETER

The present invention relates in general to new and improved densitometers and in particular to a densitometer of the vibrator type which measures the density of the substance in which it is immersed.

BACKGROUND OF THE INVENTION

Densitometers of the vibrator type which are immersed in a liquid or other substance whose density is to be measured are known in the art. Such instruments have been developed for various uses and are exemplified by the liquid densitometer disclosed in U.S. Pat. No. 4,129,031 to Stephen W. Tehon et al, which is assigned to the assignee of the present application. As shown in the patent, a pair of cylinders, positioned on a common axis, is attached to opposite ends of a compliant torsion spring supported at its nodal point intermediate the spring ends. Each cylinder has structurally defined spaces through which the ambient liquid may pass when the spring mass system is immersed therein.

First and second pairs of transducers are positioned near the opposite ends of the spring. Each transducer is capable of converting between different forms of energy or energy domains, i.e. from stored potential energy produced by the physical distorsion of the transducer, to electrical energy and vice versa. The application of a first electrical signal to the first transducer pair produces distortion in each of these transducers, which is transmitted through the spring to the second transducer pair. The second transducer pair responds by generating a second signal whose amplitude and polarity depends on the magnitude and direction of the distortion of these transducers. The second signal is amplified and applied to the first transducer pair so as to set up a regenerative loop which oscillates at the natural resonant frequency of the spring mass system. Since the liquid contained in the cylinder spaces of the immersed apparatus is part of the overall spring mass system, the frequency of oscillation is a measure of the density of the liquid in the spaces.

While the system disclosed in the referenced patent represents a substantial advance in the densitometer art over systems theretofore available for carrying out such measurements, it nevertheless includes areas susceptible of further improvement. Thus, the size of the transducers is determined by the dimensions of the torsion spring, which is seen to be a compliant bar. The size of the bar is determined by the desired parameters of the spring mass system and its cross-sectional dimensions must generally be kept small. The transducers are therefore likewise limited in size and hence their impedance is low. This results in a low signal-to-noise ratio which is improved somewhat by using a pair of transducers at each spring end. The manner in which the transducers are positioned on the bar spring subjects them to only a portion of the torsional load to which the bar spring itself is subjected. Thus, the position of the transducers in the instrument shown in the referenced patent is another factor which contributes to keeping the maximum obtainable output signal small.

In a practical example of a densitometer of the type shown in the patent, the impedance of a single transducer was on the order of 50 pf. The obtainable output signal is correspondingly low, e.g. around 50 mv when the transducer is driven at 20 volts peak-to-peak. Thus, under high noise condition, for example when the densitometer measures the density of the fuel in the wing fuel tank of an aircraft, the low signal-to-noise ratio may affect closed loop performance.

Another such area in prior art densitometers of the type under discussion here arises from the fact that the transducers contribute to the spring effect by being directly positioned on the spring. Since the transducer modulus of elasticity is sensitive to temperature changes, the spring modulus of elasticity will then also vary with temperature. If the temperature range to which the instrument is subjected varies widely, e.g. from $-50°$ C. to $+60°$ C. when the densitometer is used in aircraft in the manner discussed above, the accuracy of the instrument over the total temperature range may be affected. Experience with some prior art vibrator type densitometers has shown that the instrument error for the temperature range given above may be on the order of $+4\%$. For critical measurements it is desirable to reduce this margin of error.

A further factor which must be kept in mind with respect to such instruments is the inherent brittleness of the transducer material. The transducers typically consist of piezoelectric ceramic material, such as lead zirconate titanate or the like, and they are preferably manufactured in flat shapes for reasons of cost as well as structural stability. Where a more intricate shape is required, such as is the case in instruments of the type shown in the patent, the fabrication costs rise correspondingly.

OBJECTS OF THE INVENTION

It is a primary object of the present invention to provide a vibrator type densitometer which is free from the disadvantages of prior art instruments.

It is another object of the present invention to provide a submersible vibrator type densitometer of improved accuracy.

It is a further object of the present invention to provide a submersible densitometer of the vibrator type which is capable of providing a high signal-to-noise ratio.

It is still another object of the present invention to provide a submersible densitometer of the vibrator type which is relatively immune to temperature variations.

It is still another object of the present invention to provide a submersible instrument for measuring the density of an isotropic substance, wherein the geometry of the transducer shape is optimized to reduce the cost of manufacture.

These and other objects of the invention, together with the features and advantages thereof, will become apparent from the following detailed specification when read in conjunction with the accompanying drawings of a preferred embodiment of the invention.

BRIEF DESCRIPTION OF THE DRAWINGS

FIG. 1 is an overall view of a preferred embodiment of the invention;

FIG. 2 is a cross-sectional view of a portion of the apparatus of FIG. 1, taken at lines 2—2.

With reference now to the drawings, a preferred embodiment of the densitometer which forms the subject matter of the present invention is illustrated in FIGS. 1 through 3. In FIG. 1 the complete instrument, designated by the reference numeral 8, is shown and is seen to comprise a mass assemblage which consists of a pair of mass configurations. More specifically, the structure consists of a torsional spring, dual fluid couplers and dual piezoelectric ceramic elements. In the preferred embodiment of the invention, the fluid couplers take the form of cylindrical sleeves 10A and 10B, positioned on a common axis 12 and spaced from each other. As shown, sleeves 10, as well as other portions of the illustrated apparatus, form substantially identical, symmetrically positioned portions of a torsional spring mass system which are designated 'A' and 'B' respectively. For the sake of simplicity, the reference numerals bear A and B suffixes only when necessary to distinguish a component from its opposite counterpart. In order to illustrate the invention with greater clarity, different component parts of the identical A and B portions are shown in phantom outline in FIG. 1.

Figure 3:
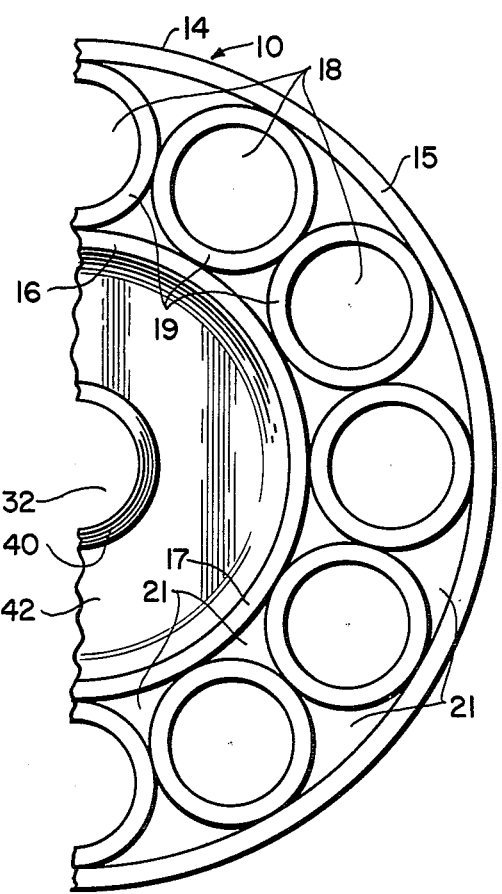
FIG. 3 is a half end view of the apparatus of FIG. 1.

As best shown in FIGS. 2 and 3, each sleeve has an outer and inner perimeter 14 and 16 respectively, the latter defining a hollow coaxial space within the sleeve. Each sleeve includes a plurality of structurally defined spaces 18, which take the form of identical numbers of cylindrical holes in the illustrated embodiment. All holes 18 extend completely through sleeves 10A and 10B respectively, in a direction parallel to axis 12. For the sake of clarity of illustration, only some of the holes in sleeve 10A are so illustrated in FIG. 1. It is preferred to construct each sleeve of a pair of radially spaced cylindrical walls 15 and 17 and to position cylindrical tubes 19 therebetween to form holes 18. The tube structure thus defines further spaces 21 which likewise extend completely through each sleeve. The liquid or other isotropic substance in which the instrument is immersed is therefore able to enter and pass through spaces 18 and 21 without obstruction to provide the desired coupling between the sleeve and the fluid. In an alternative embodiment, each sleeve 10 may be formed of a solid material between its outer and inner perimeters 14 and 16 respectively. In the latter case, holes 18 are bored or otherwise formed in the solid material, parallel to the axis. In either form of construction, each sleeve has a precisely determined fixed moment of inertia, as determined by its mass and its radius, to which is further added the small moment of inertia of hub 38. Since the fluid coupling of the sleeve is determined by the configuration of the sleeve, there also exists a fixed relationship for any particular fluid between sleeve inertia and the inertia of the fluid coupled thereto.

A torsion spring is coupled to sleeves 10A and 10B and takes the form of a coaxially positioned hollow tube in the preferred embodiment, having a predetermined torsional spring constant. A single compliant tube is shown in the drawings, having symmetrical halves on opposite sides of a nodal mount 22 which is integral with the tube. Alternatively, a pair of separate compliant tubes may be fastened to opposite sides of the nodal mount. The mount itself is seen to be disc-shaped in form. The plane of the disc lies in a plane normal to axis 12 and is centrally positioned between opposite ends of spring 20. The rim of disc-shaped nodal mount 22 is concave, as shown at 24, adapted to accept an O-ring 26. The nodal mount itself is adapted to be held in position between the clamping portions of a mounting fixture which forms no part of the present invention. Thus, the entire spring mass system is adapted to be supported solely by its nodal mount so as to be free to oscillate around axis 12. The densitometer is preferably held in an upright position so that bubbles in the liquid in which the instrument is immersed are purged.

The opposite ends of the tube which constitutes torsion spring 20 each comprise an integral flange 28. Each flange includes a flange surface 30 substantially normal to axis 12 and concentric therewith, which faces outward from the centrally located nodal mount 22. Each spring end further includes a shaft 32 integral with flange 28 and extending axially outward from flange surface 30. Shaft 32 terminates in a externally threaded shaft portion 34 adapted to accept a threaded nut 36.

Each cylindrical sleeve 10 is supported on a coaxial hub 38 which is either integral with the sleeve, i.e. integral with cylindrical wall 17 thereof, or fast therewith. Each hub is located within the hollow space defined by inner perimeter 16 and it includes a bonding surface 40. The latter surface is substantially normal to axis 12 and concentric therewith and it faces inward toward the nodal mount. Thus, at each end of torsion spring 20 a pair of mutually facing surfaces 30, 40 is located. Hub 38 further includes an axial bore 46 of a diameter adapted to make a sliding fit with shaft 32. Bore 46 extends completely through hub 38, including the aforementioned bonding surface 40.

Each cylindrical sleeve 10, together with its associated hub 38, forms a discrete mass configuration within the overall torsional spring mass system, which has its center of gravity positioned on axis 12. Each of these mass configurations is connected to torsion spring 20 by means of a mechanically stiff coupling that includes a thin, flat, disc-shaped, ceramic transducer 42. Each transducer 42 has a thickness of the order of 0.050" and an axial bore adapted to accept shaft 32. Further, each transducer is metalized on each face and is fastened to its corresponding bonding surface 40 on hub 38 by means of a bonding agent such as solder, epoxy or the like, which establishes a substantially rigid bond between the transducer and the bonding surface. A thin, flat washer 48, which is substantially coextensive with its corresponding transducer, is interposed between the latter and each flange surface 30. Each washer preferably consists of a ceramic insulating material, metalized on each face and having an overall thickness of the order of 0.050". The washers are bonded in a manner similar to transducers 42. In the preferred embodiment of the invention each washer is undercut as shown in FIG. 2, to allow room for an electrical interconnection to the high voltage side 45 of each piezoelectric transducer 42. The interconnection path leads via hole 43 and slot 44 to remote electronic circuitry illustrated in FIG. 4.

Internally threaded nut 36, which engages the threaded shaft end 34, urges the contacting hub 38 in the direction of flange surface 30 to place transducer 42 and washer 48 under compression therebetween. Nut 36 is tightened sufficiently to maintain a compressive load on transducer 42 and on washer 48 under all load conditions. Thus, a mechanically sound and torsionally stiff coupling is established between flange 28 and hub 38 and hence between torsion spring 20 and each cylindrical sleeve 10. Stated differently, the natural resonant frequency of the coupling is very high with respect to the natural torsion resonant frequency of the spring mass system. Such mechanical stiffness requires that the component parts of each coupling, i.e. transducer 42 and washer 48, be selected to be individually mechanically stiff, i.e. to have a high natural resonant frequency with respect to the torsion frequency of the spring mass system. In the present context where stiffness is considered with respect to resistance to torsion, such stiffness is a function of the torsion modulus of elasticity of the materials of the transducers and washers respectivley, as well as their diameters. In a preferred embodiment of the invention, transducers 42 consist of a piezoelectric ceramic material and washers 48 consist of an alumina ceramic material. Both have a large enough diameter to be substantially stiff relative to the torsional stiffness of torsion spring 20.

Each transducer is capable of converting between the respective domains of electrical signal energy and potential energy, the latter being created by the deformation of the transducer. As will become clear from the discussion below, one of the transducers, i.e. sensing transducer 42A, is used in a manner whereby it provides an electrical signal whose amplitude and polarity depend on the magnitude and direction of the torsional distortion of the transducer. Driving transducer 42B provides torsional distortion corresponding in magnitude and direction to the amplitude and polarity of a signal applied to this transducer.

Figure 4:
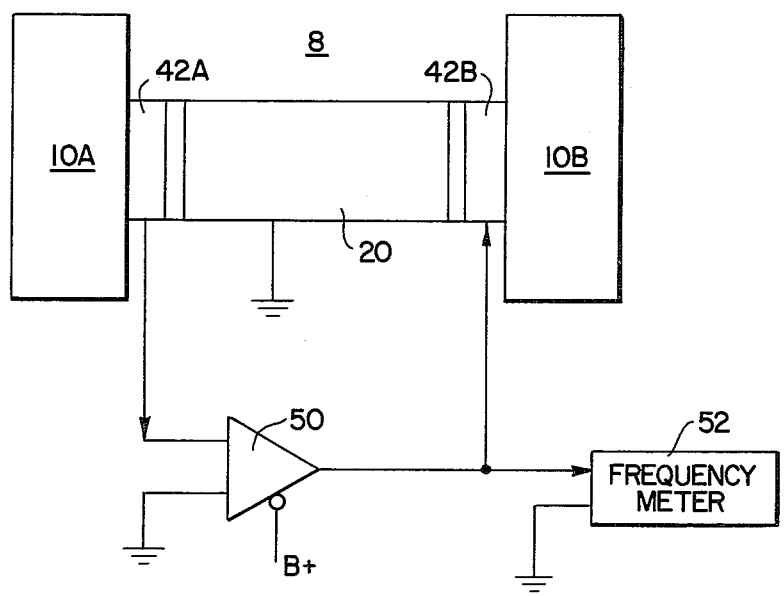
FIG. 4 is a schematic diagram of a measuring circuit which incorporates the apparatus of FIGS. 1 through 3.

FIG. 4 illustrates a preferred measuring circuit which utilizes the instrument shown in FIGS. 1 through 3. Densitometer 8 is shown with sensing transducer 42A and driver transducer 42B positioned at opposite ends of torsion spring 20. These transducers form the electrical output and input respectively of the instrument. The output of sensing transducer 42A is connected to the input of an amplifier 50 and is adapted to apply a voltage thereto referenced to ground. Amplifier 50, which further receives a B+ voltage, has its output connected to the input of driver transducer 42B in a manner adapted to form a regenerative loop. The amplifier output is further connected to a frequency meter 52.

In operation, when a voltage is applied to the terminals of driver transducer 42B, the latter undergoes torsional distortion around axis 12. The magnitude and direction of this distortion correspond to the amplitude and polarity respectively, of the signal applied to transducer 42B. In a practical embodiment of the invention, the distortion was less than one milliradian for an applied voltage of 10 volts peak to peak. Since transducer 42B is fastened to one of hubs 38 by way of bonding surface 40, the distortion of the transducer results in an angular displacement of mass configuration B, i.e. sleeve 10B and its corresponding hub. Such displacement imparts angular acceleration to mass configuration B and causes torsion spring 20 to twist with respect to nodal mount 22. This dynamic action serves to apply a torsional shear torque to sensing transducer 42A, which provides a responsive signal corresponding in amplitude and polarity to the magnitude and direction respectively, of the applied torque. As stated above, the signal provided by transducer 42A is amplified and is regeneratively applied to transducer 42B to produce oscillation of the overall spring mass system. The gain of amplifier 50 is selected to sustain this oscillation of the system at its natural resonant torsion frequency.

As stated above, the mass of each sleeve 10 (which includes the mass of hub 38), together with the sleeve radius, determines the moment of inertia of the sleeve and is precisely determined. When the sleeve is immersed in a fluid or other isotropic substance, the resultant moment of inertia includes whatever portion of the fluid is coupled to the sleeve, i.e. the fluid contained in the structurally defined spaces 18 and 21 of each cylinder, or in spaces 18 only where the alternative configuration is used. The portion of the fluid contained in these spaces thus forms part of mass configurations A and B respectively, which jointly constitute the overall spring mass system together with torsion spring 20. The ratio of fluid mass to sleeve mass is selected as large as possible, but it is limited by practical considerations. In an actual embodiment of the invention this ratio was approximately 1:4. Since the mass of the fluid contained in spaces 18 and 21 is a function of fluid density, the latter directly affects the natural resonant frequency of oscillation of the system. Thus, the frequency measured by frequency meter 52 is a direct function of the density of the liquid in which the instrument is immersed.

As best shown in FIG. 3, each transducer 42 comprises a disc-shaped, flat wafer with an axial opening adapted to receive shaft 32. The area of the disc is seen to be relatively large. Since electrical impedance varies directly with area, transducer 42 presents a relatively high impedance which minimizes circuit loading attenuation effects. As a consequence, the output signal provided is high compared to that obtainable in prior art apparatus. In an actual embodiment of the invention, transducer impedance was on the order of 500 pf. When the transducer was driven 10 volts peak-to-peak and a 1 megohm load was used, a 7 volt peak-to-peak output signal was obtained. By comparison, prior art instruments of the type shown in the aforesaid patent have a transducer impedance of the order of 50 pf. Using the same load resistance, a maximum output signal no greater than 50 millivolt is obtainable for a 20 volt peak-to-peak excitation. If the noise coupled through to the signal remains substantially constant as the signal increases in amplitude, the larger output signal obtainable with the present invention provides a higher signal-to-noise ratio. Thus, the closed loop stability of the instrument is high. A still higher output signal level is possible by scaling up the dimensions of the respective component portions of the instrument shown in FIGS. 1 through 3. Alternatively, the geometry of the instrument with respect to the location of the hub may be rearranged so that bonding surfaces 40 are positioned clear of sleeves 10 in an axial direction. In such an arrangement the area of the transducer disc may be increased without changing the dimensions of the other parts of the configurations.

Since transducer impedance varies inversely with transducer thickness, it is desirable to keep the latter dimension small. In prior art densitometers of the kind shown in the above-referenced patent, this is possible only to a point due to the nature of the transducer configuration, the exposed position of the transducer and the inherent brittleness of the transducer material. It is a feature of the present invention to provide an instrument in which the transducers take the form of thin flat wafers. With such a transducer shape a much smaller thickness dimension is possible, notwithstanding the brittleness of the material. Moreover, since the transducer is axially loaded as threaded nut 36 is tightened against hub 38, the vulnerability of the densitometer through damage to the transducers is greatly reduced. It must also be kept in mind that the axial compression of the transducer reduces the chance of cracks developing in the transducer material. Thus, for a given thickness, restrictions on the size of the transducer area are either eliminated or minimized in the present invention. Of equal importance is the considerable reduction in the cost of manufacture of the transducers, owing to their greatly simplified configuration.

In the present invention, the position of each transducer is such that it takes substantially the full torsional shear load between the corresponding sleeve 10 and torsion spring 20. Therefore, as compared to prior art instruments, transducer distortion is maximized upon oscillation of the spring mass system. Hence, the obtainable output signal is further increased as a consequence of transducer position alone.

As previously explained, the stiffness of the transducer, i.e. its natural resonant frequency, is high compared to that of the torsion spring. This property, coupled with the position of the transducer between the spring and each mass configuration, assures that the transducer acts only as a stiff intervening layer without contributing materially to the torsional spring effect. Thus, whatever the sensitivity to temperature changes of the piezoelectric ceramic transducer material may be, it has no significant effect on the spring. In a practical embodiment of the invention, using typical aircraft fuels, the error due to temperature sensitivity of the instrument was reduced to less than 1% of full scale over a temperature range from −50° C. to +60° C.

Various modifications of the disclosed apparatus are feasible within the scope of the present invention. For example, the torsion spring need not be a compliant tube and may take a number of other forms. Further, as discussed above, various changes of the geometry of the disclosed apparatus may be made for the purpose of increasing the transducer area and hence transducer impedance. Such modifications may be carried out without detriment to the other features and advantages of the present invention, such as transducer positioning to carry substantially the full torsional shear load while remaining substantially stiff relative to the spring effect of the system; axial compression loading of the transducers which permits the use of a thin wafer of the brittle transducer material having a large surface area; the use of a simple transducer configuration in order to reduce manufacturing costs; etc.

From the foregoing discussion of a new and improved densitometer of the torsional vibrator type, it will be apparent that numerous variations, modifications, changes and equivalents will now occur to those skilled in the art, all of which fall within the spirit and scope of the present invention. Accordingly, it is intended that the invention be limited only by the scope of the appended claims.

What is claimed is:

1. An instrument for measuring the density of an ambient substance having substantially isotropic properties;

said instrument comprising:

spring means positioned to permit torsional deformation thereof around an axis;

a mass assemblage having its center of gravity positioned substantially on said axis, said mass assemblage including structurally defined spaces radially spaced from said axis and open to said ambient substance; and mechanically stiff coupling means connecting said mass assemblage to said spring means to form a torsional spring mass system including the mass of said ambient substance contained within said spaces, said system being capable of oscillatory motion around said axis at a natural resonant system torsion frequency dependent on the density of the ambient substance contained in said spaces;

the respective natural resonant torsion frequencies of said coupling means and of said mass assemblage being selected to be high with respect to said natural resonant system torsion frequency;

said coupling means including transducer means adapted to convert between electrical energy and potential energy stored as deformation around said axis, the natural resonant torsion frequency of said transducer means being selected to be high with respect to the natural resonant torsion frequency of said spring means, said transducer means being located at the torsion shear interface between said spring means and said mass assemblage substantially normal to said axis, said transducer means being positioned to take substantially the full shear load between said spring means and said mass assemblage while remaining substantially stiff relative to the spring effect of said system;

whereby said instrument is substantially immune to temperature variations affecting said transducer means.

2. Apparatus in accordance with claim 1 wherein said mass assemblage comprises first and second discrete mass configurations, each of said mass configurations including between its outer perimeter and said axis a plurality of said structurally defined spaces and a bonding surface substantially normal to said axis, said spaces and said bonding surface in each of said mass configurations being positioned at mutually different radial distances from said axis;

said spring means comprising a torsion spring having opposite ends thereof connected to respective ones of said mass configurations through separate ones of said coupling means;

each of said separate coupling means including a separate one of said transducer means fastened to the bonding surface of the connected mass configuration, each of said separate transducer means having a high electrical impedance and being adapted to take substantially the full shear load between the corresponding mass configuration and said torsion spring;

a first one of said transducer means being responsive to the magnitude and direction of deformation around said axis imposed thereon to provide a first electrical signal having a corresponding amplitude and polarity respectively; and a second one of said transducer means being responsive to the amplitude and polarity of an applied second signal to produce deformation thereof around said axis having a corresponding magnitude and direction respectively.

3. Apparatus in accordance with claim 2 wherein said first and second mass configurations have their respective centers of gravity positioned on said axis mutually spaced from each other; and wherein said torsion spring has an elongate configuration extending substantially along said axis.

4. Apparatus in accordance with claim 3 wherein said structurally defined spaces are open to the flow of said ambient substance in an axial direction.

5. Apparatus in accordance with claim 4 wherein each of said mass configurations includes an axially mounted cylinder adapted to oscillate around said axis, said spaces being symmetrically positioned in said cylinder with respect to said axis and extending parallel to the latter.

6. Apparatus in accordance with claim 5 wherein said cylinders form substantially identical cylindrical sleeves each having a predetermined radial thickness between said outer perimeter and an inner perimeter defining a hollow cylindrical core;

said spaces in each of said sleeves comprising a plurality of tubular holes extending the full length of said sleeve and being positioned at a substantially uniform spacing around said axis; and each of said mass configurations further including a hub fast with the corresponding sleeve inside the hollow core thereof, each of said hubs including one of said bonding surfaces concentric with said axis and radially spaced therefrom.

7. Apparatus in accordance with claim 3 or 6 wherein each of said transducer means comprises a single piezoelectric ceramic transducer in the form of a flat disc fastened to its corresponding bonding surface and substantially coextensive therewith.

8. Apparatus in accordance with claim 3 wherein said torsion spring comprises a hollow tube mounted at a nodal point centrally between said opposite spring ends, each of said opposite spring ends comprising a flange including a flange surface substantially normal to said axis and concentric therewith;

each of said mass configurations comprising a hub each including one of said bonding surfaces concentric with said axis and radially spaced therefrom, each of said bonding surfaces facing one of said flange surfaces;

each of said transducer means comprising a piezoelectric ceramic transducer in the form of a flat disc substantially coextensive with the bonding surface to which it is fastened;

each of said coupling means further including a washer in the form of a flat disc disposed between each of said flange surfaces and a corresponding one of said transducers; and means for holding one of said transducers and its adjacent washer in axial compression between each pair of said facing surfaces.

9. Apparatus in accordance with claim 8 wherein said mass configurations are substantially identical, each mass configuration further comprising a cylindrical sleeve coaxially surrounding a corresponding one of said hubs and fast therewith;

each of said sleeves having a predetermined radial thickness between said outer perimeter and an inner perimeter and being positioned in mutually spaced coaxial relationship with respect to the other sleeve; and said spaces in each of said sleeves comprising a plurality of tubular holes extending the full length of said sleeve parallel to said axis and positioned substantially uniformly around the latter at a constant radial distance therefrom.

10. Apparatus in accordance with claim 9 wherein each of said hubs, said transducers and said washers includes an axial bore, one of each of said hubs, said transducers and said washers respectively being coaxially disposed at each spring end with said bores substantially in registry with each other;

each of said spring ends including a shaft extending axially outward from said flange surface and engaging said registering axial bores, each of said shafts including a free shaft end remote from said flange surface; and said compression holding means comprising a nut threadedly engaging each of said free shaft ends to urge the bonding surface of the contacting hub toward its facing flange surface.

11. Apparatus in accordance with claim 3 or 10 and further including amplifier means responsive to said first signal to provide said second signal at the output thereof;

means for coupling said second signal to said second transducer means in a manner adapted to form a regenerative loop, said amplifier means having a gain sufficient to sustain said oscillatory motion of said spring mass system at said natural resonant system torsion frequency; and means for measuring the frequency of said second signal as a representation of said natural resonant system torsion frequency;

whereby said second signal has a high signal-to-noise ratio and is adapted to provide a large frequency variation as a function of density change of said ambient substance substantially independent of temperature variations affecting said transducer means.

12. An instrument for measuring the density of an ambient liquid comprising:

first and second mass configurations having respective centers of gravity mutually spaced along a common axis;

each of said mass configurations including between its outer perimeter and said axis a bonding surface substantially normal to said axis and a plurality of structurally defined spaces adapted to permit the flow of said liquid therethrough in a direction substantially parallel to said axis;

an elongate torsion spring extending substantially in an axial direction between said bonding surfaces;

nodal mounting means for supporting said torsion spring intermediate opposite ends thereof;

separate, mechanically stiff coupling means connecting each of said bonding surfaces to one of said spring ends to form a torsional spring mass system including the ambient liquid portion contained within said spaces, said spring mass system being capable of oscillatory motion around said axis at a natural resonant system torsion frequency dependent on the density of said liquid;

the respective natural resonant torsion frequencies of said mass configurations and of said coupling means being selected to be high with respect to said natural resonant torsion frequency of said system;

each of said coupling means including transducer means fastened to one of said bonding surfaces in a manner adapted to take substantially the full torsional shear load between the corresponding mass configuration and said spring while remaining substantially stiff relative to the spring effect of said system;

each of said transducer means having a natural resonant torsion frequency selected to be high with respect to the natural resonant torsion frequency of said spring;

one of said transducer means being adapted to provide a first signal in response to the magnitude and direction of deformation imposed thereon around said axis;

the other transducer means being adapted to produce deformation around said axis in response to the amplitude and polarity of an applied second signal;

amplifier means responsive to the application of said first signal to provide said second signal at the output thereof;

means for coupling said second signal to said second transducer means to form a regenerative loop, said amplifier means providing a loop gain sufficient to sustain the oscillations of said spring mass system around said axis at said system frequency; and means for determining the frequency of said second signal as a measure of the density of said ambient liquid;

whereby said system is adapted to provide said second signal at a high signal-to-noise ratio, said second signal having a high frequency variation as a function of change of density of said ambient liquid substantially immune to temperature variations affecting said transducer means.

13. Apparatus in accordance with claim 12 wherein each of said transducer means comprises a thin disc of piezoelectric material, said disc having a large surface area substantially coextensive with its corresponding bonding surface and being adapted to provide a high electrical impedance.

14. Apparatus in accordance with claim 13 wherein each of said spring ends includes a flange surface facing one of said bonding surfaces; and means for holding said coupling means in axial compression between each pair of facing surfaces.

15. An instrument for measuring the density of an ambient liquid; said instrument comprising:

a hollow tube including a nodal point intermediate opposite ends thereof, said tube having a predetermined torsion spring constant adapted to permit torsional deformation around the tube axis relative to said nodal point;

said opposite tube ends each including a flange having a flange surface substantially normal to said axis and facing outward with respect to said nodal point;

each of said tube ends further including a shaft extending axially outward from a corresponding one of said flange surfaces;

mounting means adapted to support said tube at said nodal point;

first and second substantially identical, cylindrical sleeves of predetermined mass each having a radial thickness defined between its inner and outer perimeters, each of said inner perimeters defining a hollow cylindrical space, said sleeves being coaxially mounted on said axis at a mutual spacing substantially determined by the length of said tube;

a plurality of tubular holes in each of said sleeves between said inner and outer perimeters open to the passage of said liquid in a direction substantially parallel to said axis, said holes being uniformly disposed around said axis at a substantially constant radial spacing therefrom;

a hub coaxially positioned within said hollow cylindrical space of each of said sleeves mounted fast with the latter, each of said hubs including an axial bore and a bonding surface concentrically surrounding said bore, each of said bonding surfaces being substantially normal to said axis and facing a corresponding one of said flange surfaces;

mechanically stiff coupling means connecting each of said bonding surfaces to its corresponding flange surface to form a torsional spring mass system, said system including the liquid contained in said spaces and being capable of oscillatory motion around said axis at a natural resonant system torsion frequency dependent on the density of said liquid;

the respective natural resonant torsion frequencies of said coupling means and of said hub-mounted sleeves being selected to be high with respect to said system frequency;

one of said coupling means including a driver transducer;

the other of said coupling means including a sensing transducer;

each of said transducers comprising a flat piezoelectric ceramic disc having an axial bore, the natural resonant torsion frequency of each of said transducers being selected to be high with respect to the natural resonant torsion frequency of said hollow tube, each of said transducers having a small thickness and a large area substantially coextensive with a corresponding one of said bonding surfaces and providing a high electrical impedance;

each of said transducers being fastened to its corresponding bonding surface to take substantially the full torsional shear load between the corresponding hub-mounted sleeve and said hollow tube while remaining substantially stiff relative to the spring effect of said system;

said sensing transducer being responsive to the magnitude and direction of deformation imposed thereon around said axis to provide a first signal of a corresponding amplitude and polarity respectively;

said driver transducer being responsive to the amplitude and polarity of an applied second signal to produce deformation around said axis of a corresponding magnitude and direction respectively;

each of said coupling means further including a pair of washers respectively comprising a flat ceramic disc having an axial bore, each of said washers being substantially coextensive with a corresponding one of said transducers and in contact therewith;

each of said shafts engaging the axial bores belonging to one of each of said transducers, said washers and said hubs respectively and including a free shaft end extending beyond the corresponding hub; and a nut threadedly engaging each of said free shaft ends, each of said nuts being adapted to place one of said coupling means in axial compression by urging the bonding surface of the contacting hub toward its facing flange surface.

16. Apparatus in accordance with claim 15 and further comprising:

amplifier means responsive to the application of said first signal to provide said second signal at the amplifier output; and means for coupling said second signal to said driver transducer to form a regenerative loop, said amplifier means providing a loop gain sufficient to sustain the oscillatory motion of said spring mass system at said natural resonant system torsion frequency;

whereby said second signal has a high signal-to-noise ratio and is adapted to provide a large frequency variation as a function of density change of said ambient liquid substantially independent of temperature variations affecting said transducers.

* * * * *